US008809773B2

(12) United States Patent
Bier

(10) Patent No.: US 8,809,773 B2

(45) Date of Patent: Aug. 19, 2014

(54) MEMBRANE INTERFACE APPARATUS AND METHOD FOR MASS SPECTROMETRY

(75) Inventor: Mark E. Bier, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 749 days.

(21) Appl. No.: 11/886,890

(22) PCT Filed: Mar. 22, 2006

(86) PCT No.: PCT/US2006/010612

§ 371 (c)(1), (2), (4) Date: Sep. 20, 2007

(87) PCT Pub. No.: WO2006/102520

PCT Pub. Date: Sep. 28, 2006

(65) Prior Publication Data

US 2009/0020696 A1 Jan. 22, 2009

Related U.S. Application Data

(60) Provisional application No. 60/664,095, filed on Mar. 22, 2005.

(51) Int. Cl.

| | |
|---|---|
| ***H01J 49/00*** | (2006.01) |
| ***B01D 59/44*** | (2006.01) |
| ***G01N 1/00*** | (2006.01) |
| *G01N 1/28* | (2006.01) |

(52) U.S. Cl.

CPC *B01D 59/44* (2013.01); *G01N 1/00* (2013.01); *G01N 1/28* (2013.01)

USPC ............................ 250/288; 250/281; 250/282

(58) Field of Classification Search

None

See application file for complete search history.

(56) References Cited

U.S. PATENT DOCUMENTS

| | | | | |
|---|---|---|---|---|
| 4,642,165 | A * | 2/1987 | Bier | 203/12 |
| 4,694,832 | A * | 9/1987 | Ungerstedt | 600/366 |
| 4,791,292 | A * | 12/1988 | Cooks et al. | 250/288 |
| 4,820,648 | A * | 4/1989 | Caprioli et al. | 436/89 |
| 4,912,051 | A * | 3/1990 | Zaromb | 436/178 |

(Continued)

FOREIGN PATENT DOCUMENTS

| | | | | |
|---|---|---|---|---|
| JP | 2004191271 A * | 7/2004 | | G01N 27/62 |
| WO | WO 9811434 A1 * | 3/1998 | | G01N 33/50 |

OTHER PUBLICATIONS

Clinton, et al.; Real-Time Monitoring of a Pharmaceutical Process Reaction Using a Membrane Interface Combined with Atmospheric Pressure Chemical Ionisation Mass Spectrometry; Analytica Chimica Acta, 539; pp. 133-140; Mar. 2005.

(Continued)

*Primary Examiner* — Andrew Smyth

(74) *Attorney, Agent, or Firm* — Jones Day

(57) ABSTRACT

The disclosed method and apparatus couple a membrane interface directly to a mass spectrometer at atmospheric pressure. The membrane may be in capillary or sheet form and allows the introduction of a liquid or gaseous sample to one side of the membrane while the other side of the membrane is bathed with a solution that can easily be used in an atmospheric pressure ionization source. Volatile molecules permeate through a suitable membrane such as poly-dimethyl silicone (PDMS), mix into the appropriate solvent, and are ionized. Because of the rules governing abstracts, this abstract should not be used in construing the claims.

16 Claims, 15 Drawing Sheets

12
$V_1$
18
14
10
21
16
20
18
14

(56) References Cited

U.S. PATENT DOCUMENTS

| | | | | |
|---|---|---|---|---|
| 5,026,987 | A * | 6/1991 | Bier et al. | 250/281 |
| 5,162,650 | A * | 11/1992 | Bier | 250/288 |
| 5,279,543 | A * | 1/1994 | Glikfeld et al. | 604/20 |
| 5,398,559 | A * | 3/1995 | Westlake et al. | 73/863.81 |
| 5,420,425 | A * | 5/1995 | Bier et al. | 250/292 |
| 5,572,022 | A * | 11/1996 | Schwartz et al. | 250/282 |
| 5,703,359 | A * | 12/1997 | Wampler, III | 250/288 |
| 5,750,993 | A * | 5/1998 | Bier | 250/282 |
| 5,756,996 | A * | 5/1998 | Bier et al. | 250/292 |
| 6,284,115 | B1 * | 9/2001 | Apffel | 204/518 |
| 6,284,117 | B1 * | 9/2001 | Smolko et al. | 204/543 |
| 6,360,588 | B1 * | 3/2002 | Ross et al. | 73/38 |
| 6,542,765 | B1 * | 4/2003 | Guy et al. | 600/345 |
| 6,638,408 | B1 * | 10/2003 | Speicher et al. | 204/458 |
| 6,918,886 | B1 * | 7/2005 | Baurmeister | 604/6.09 |
| 2002/0081231 | A1 * | 6/2002 | Shapiro et al. | 422/68.1 |
| 2003/0211629 | A1 * | 11/2003 | Baumgardner et al. | 436/173 |
| 2005/0087445 | A1 * | 4/2005 | Speicher et al. | 204/450 |
| 2006/0131235 | A1 * | 6/2006 | Offeman et al. | 210/640 |

OTHER PUBLICATIONS

Li, et al.; Miniaturized Membrane-Based Reversed-Phase Chromatography and Enzyme Reactor for Protein Digestion, Peptide Separation, and Protein Identification Using Electrospray Ionization Mass Spectrometry; Journal of Chromatography A, 979; pp. 241-247; 2002.

Jiang and Lee; On-Line Coupling of Micro-Enzyme Reactor with Micro-Membrane Chromatography for Protein Digestion, Peptide Separation, and Protein Identification Using Electrospray Ionization Mass Spectrometry; Journal of Chromatography A, 924; pp. 315-322; 2001.

Cooper, et al.; Membrane-Based Nanoscale Proteolytic Reactor Enabling Protein Digestion, Peptide Separation, and Protein Identification Using Mass Spectrometry; Analytical Chemistry, vol. 75, No. 5; pp. 1067-1074; Mar. 2003.

Nelson, et al.; Monitoring the TiO2-Photocatalyzed Destruction of Aqueous Environmental Contaminants at Parts-Per-Trillion Levels Using Membrane Introduction Mass Spectrometry (MIMS); Journal of Environmental Science and Health, Part A, Toxic/Hazardous Substances & Environmental Engineering; vol. A39, No. 9; pp. 2307-2317; 2004.

Ketola, et al.; Environmental Applications of Membrane Introduction Mass Spectrometry; Journal of Mass Spectrometry, 37(5); pp. 457-476; 2002.

Kotiaho, Tapio, Lauritsen, Frants; Membrane Inlet Mass Spectrometry; Comprehensive Analytical Chemistry, 37; pp. 531-557; 2002.

Riter, Leah, Takats, Zoltan, Charles, Laurence, Cooks, R. Graham; High Surface Area Membrane Introduction Mass Spectrometry for Analysis of Volatile and Semi-Volatile Organic Compounds in Air; Rapid Communications in Spectrometry, 15(17); pp. 1520-1524; 2001.

Cooks, R. Graham; Takats, Zoltan, Augusti, Rodinei, Turowski, Maciej, Ritter, Leah; Process Mass Spectrometry Using Miniature Traps and Membrane Introduction; Abstracts of Papers, 222nd ACS National Meeting, Chicago, IL; Aug. 2001.

* cited by examiner

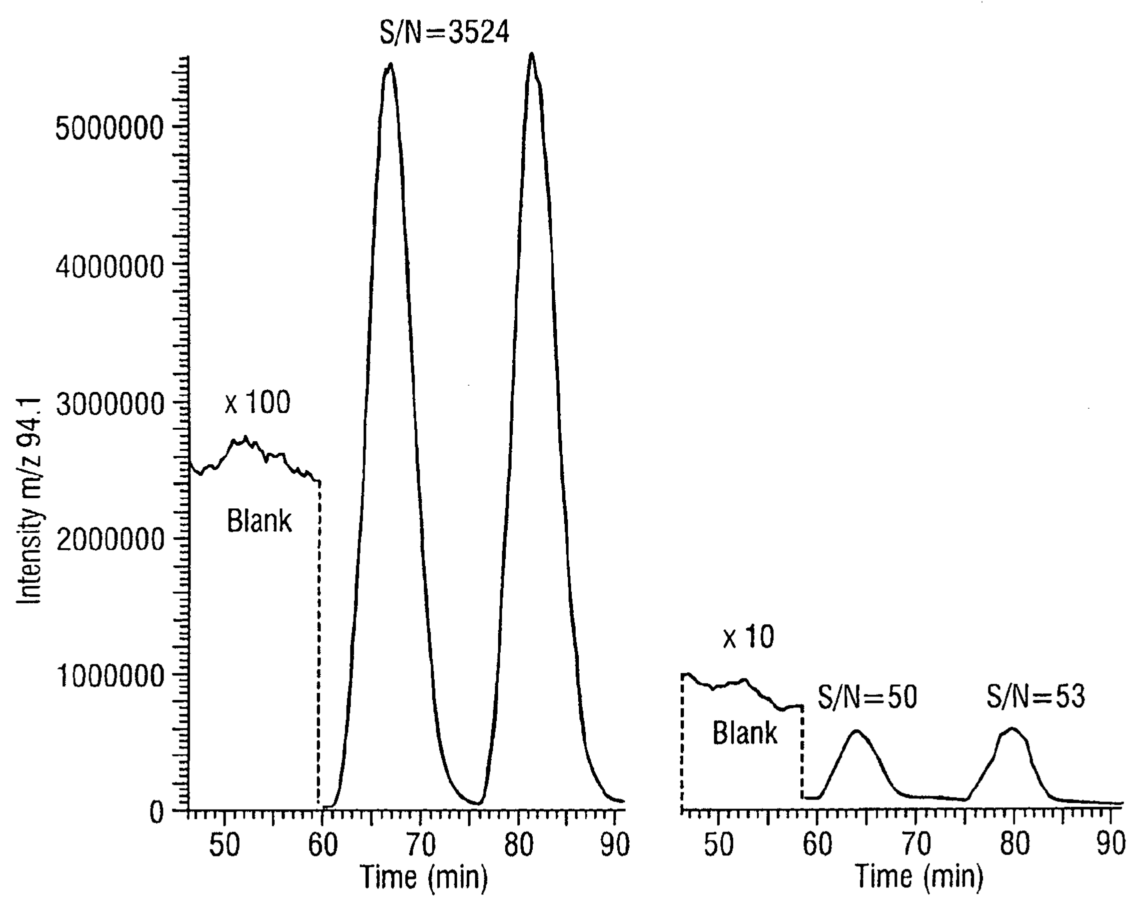
*Fig.6A* *Fig.6B*

MEMBRANE INTERFACE APPARATUS AND METHOD FOR MASS SPECTROMETRY

This application claims priority from U.S. provisional application Ser. No. 60/664,095 filed Mar. 22, 2005 and entitled Membrane Interface Apparatus and Method of Analysis of Volatile Molecules by Mass Spectrometry, the entirety of which is hereby incorporated by reference, now expired, and copending PCT/US2006/010612 filed Mar. 22, 2006 and entitled Membrane Interface Apparatus and Method of Analysis of Volatile Molecules by Mass Spectrometry, the entirety of which is hereby incorporated by reference.

BACKGROUND

The present invention is directed to membrane introduction devices coupled to a mass spectrometer to introduce volatile molecules in solution into the ion source. Most of that work has coupled a membrane interface to an electron ionization (EI) or chemical ionization (CI) source. As a result, the volatile molecules that permeate the membrane go under a pervaporization process on the other side of the membrane where they are desorbed from the membrane surface and can then be ionized in the gas phase. For more detailed information please see Mark Bier's Ph.D. Thesis, Purdue University 1988 (incorporated herein by reference).

Membrane introduction mass spectrometry (MIMS) is a sensitive, selective technique for the analysis for many small organic compounds in water in real-time. In this technique, small molecules are selectively concentrated by adsorption and separated from the water by preferential permeation through a membrane.

First used by Hoch and Kok (see A Mass Spectrometer Inlet System for Sampling Gases Dissolved in Liquid Phases. *Arch. Biochem. Biophys.* 1963, 101(1), 160-170) as a method for monitoring the production and consumption of gases during photosynthesis, MIMS has since been developed as a versatile analytical method that is applicable to a wide variety of analyses. For example, MIMS has been used to monitor the ethanol content of a fermentation broth, biological reactions, the destruction of environmental contaminants, the chlorination of organic amines in water, kinetic and mechanistic aspects of chlorination of organic compounds in water, organometallic compounds in water, and volatile and semi-volatile organic compounds (VOC and SVOC) in a variety of matrices. Most VOCs have been analyzed by MIMS in air or in aqueous solution, but they have also been analyzed in soil and human breath.

There are many methods available to analyze VOC and SVOC in water such as headspace analysis and purge-and-trap coupled to gas chromatography (GC) or gas-chromatography-mass spectrometry (GC-MS). Headspace analysis requires little time for sample preparation, but generally can be used only for contaminants at high concentrations. Purge-and-trap analysis is a recommended concentrating method by the Environmental Protection Agency (EPA), but it often has problems of sample carryover and contamination and it is also an expensive method that requires a bulky apparatus. Liquid-liquid extraction, and solid-phase micro extraction are commonly used for analyzing SVOCs. Liquid-liquid extraction methods generally require large quantities of solvents which makes them more expensive and less environmentally friendly. Solid-phase micro extraction, while fast compared to some other methods mentioned here, can require tens of minutes of off-line sample preparation prior to analysis and requires an individual solid phase concentrating cartridge per sample.

Early MIMS systems were plagued with problems of irreproducibility, membrane memory effects, long response times and high detection limits (see Johnson, R. C.; Cooks, R. G.; Allen, T. M.; Cisper, M. E.; Hemberger, P. H. Membrane Introduction Mass Spectrometry: Trends and Applications. *Mass Spectrometry Reviews.* 2000, 19(1), 1-37). To effectively analyze low level environmental contaminants, design improvements have been made to these devices. For example, a direct insertion membrane probe was built to place a capillary membrane directly inside the ionization source of a mass spectrometer located millimeters from the electron ionizing beam (see Bier, M. E.; Cooks, R. G. Membrane Interface for Selective Introduction of Volatile Compounds Directly into the Ionization Chamber for a Mass Spectrometer. Anal. Chem. 1987, 59(4), 597-601). The close proximity of the membrane to the ionization region allowed for rapid reproducible analysis of VOCs in water at low detection limits with minimal memory effects because the analyte was instantaneously ionized with little mixing rather than flowing inside a transfer line and the membrane was heated to increase permeation rates. In 1991, Silvon et al. developed a helium-purged hollow fiber membrane interface that allowed for detection at the sub part-per-billion (ppb) levels in the analysis of VOCs and SVOCs (see Silvon, L. E.; Bauer, M. R.; Ho, J. S.; Budde, W. L. Helium-Purged Hollow Fiber Membrane Mass Spectrometer Interface for Continuous Measurement of Organic Compounds in Water. *Anal. Chem.* 1991, 63(13), 1335-1340). In Silvon's device, a capillary membrane is placed inside a flow cell with a helium purge running through the membrane to the mass spectrometer while the aqueous sample runs outside the membrane in the opposite direction. The best detection limit has come from Soni et. al. who detected 500 parts per quadrillion (ppq) of toluene with a S/N 11 with data point smoothing (see Soni, M. H.; Baronavski, A. P.; McElvany, S. W. Trace Analysis of Polyaromatic Hydrocarbons in Water Using Multiphoton Ionization-Membrane Introduction Mass Spectrometry. *Rapid Commun. Mass Spectrom.* 1998, 12, 1635-1638). In this experiment, a stored wave form inverse Fourier transform (SWIFT) signal was applied to the end caps of a 3D quadrupole ion trap. The SWIFT waveform isolates desired analyte ions by ejecting only those contaminant ions at the frequencies in the SWIFT signal. The use of this waveform and other similar waveforms allowed for a significant concentration of the ions of interest.

Finally, U.S. Pat. No. 6,360,588 to Ross et al. discloses an efficient and accurate method and apparatus for analysis of materials passing through a membrane. A sample is place on one side of a membrane and a carrier fluid from a reservoir flows past the other side of the membrane to carry any sample diffusing through the membrane to be detected. The disclosed method can allow for the accurate, precise, and specific real time measurements of compounds crossing a membrane.

BRIEF SUMMARY OF THE DISCLOSURE

According to one embodiment of the probe of the present disclosure, the probe is comprised of a first flow path, a second flow path defined by a membrane, the membrane separating the first and second flow paths, and a needle integrated with the membrane so as to form a part of the second flow path. In one embodiment of the method of the present disclosure, a method of operating a probe is comprised of flowing a material in a first flow path, flowing a fluid in a second flow path defined by a membrane, the first and second flow paths separated by the membrane, and transferring the fluid at the end of the second flow path to an ionization region of a mass spectrometer through a needle.

In the disclosed embodiments of the apparatus and methods of the present disclosure, the carrier of the analyte to the ionization region is a liquid. The disclosed embodiments of the apparatus and methods allow for the coupling of a membrane interface directly to a mass spectrometer at atmospheric pressure. The membrane can be in capillary or sheet form and allows the introduction of a liquid or gaseous sample to one side of the membrane while the other side of the membrane is bathed with a solution that can easily be used in an atmospheric pressure ionization source. Volatile molecules permeate through a suitable membrane such as poly-dimethyl silicone (PDMS), mix into the appropriate solvent, and are ionized. The probe can be heated or cooled, various additives may be added to either side of the membrane, or a voltage potential may be impressed across the membrane to improve performance.

BRIEF DESCRIPTION OF THE DRAWINGS

For the present disclosure to be easily understood and readily practiced, the present disclosure will now be described, for purposes of illustration and not limitation, in conjunction with the following figures wherein:

FIGS. 6A and 6B are a comparison of the signal intensity of the mass chromatogram of 1 ppm aniline in water, m/z 94.1, using the probe of the present disclosure compared to the LCQ standard ESI source with no membrane, respectively;

FIGS. 16A and 16B illustrate embodiments according to the teachings of the present invention using multiple membranes with an EI/CI source in FIG. 16A and an ESI source in FIG. 16B; and.

DETAILED DESCRIPTION

Figure 1A:
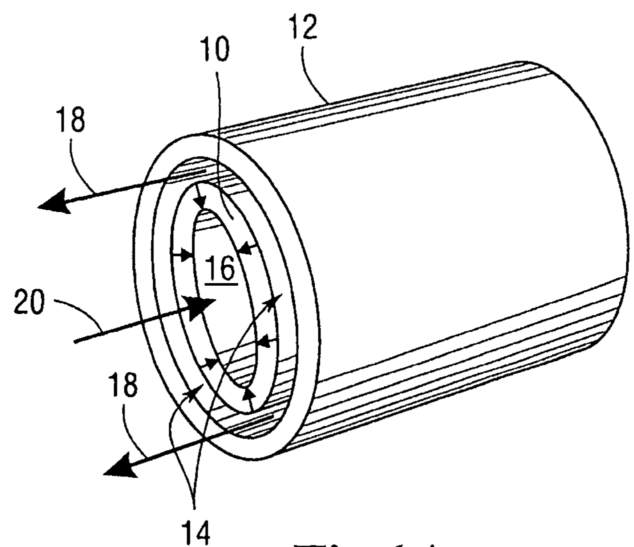
FIGS. 1A and 1B illustrate embodiments of the present disclosure using a tubular capillary membrane fitted inside a stainless steel tube; mobile phase 1 travels within the space between the outside diameter of the membrane and the inside diameter of the steel tube while mobile phase 2 travels within the space within the center of the membrane.
Figure 1B:
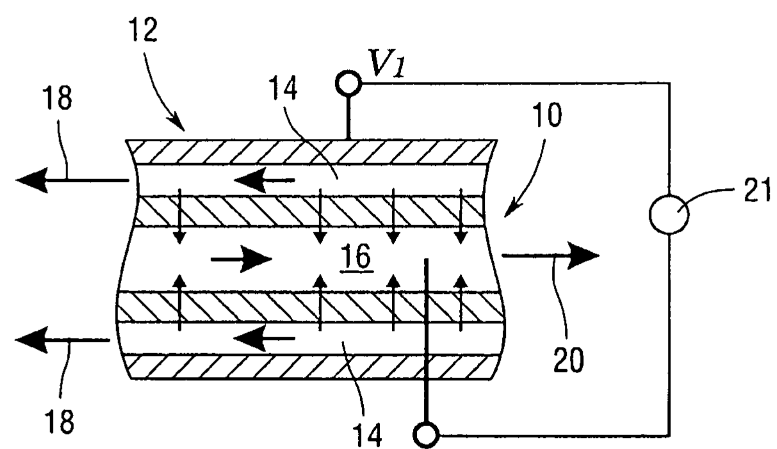

FIGS. 1A and 1B illustrate one embodiment of the device of the present disclosure. In the figures, a capillary membrane 10 in the shape of a tube is fitted within a stainless steel tube 12. A space or channel 14 is formed between the outside diameter of the membrane 10 and the inside diameter of the steel tube 12. Another space or channel 16 is formed inside of tubular membrane 10. Mobile phase 1 (i.e. the phase that carries the analyte to the membrane) travels within space 14 as shown by the arrows 18. Mobile phase 2 (i.e. the phase that carries the analyte away from the membrane to an ionization region) travels within space 16 as shown by arrow 20.

Volatile organics in mobile phase 1 are adsorbed onto and permeate through the membrane 10 and are then removed at the other side of the membrane 10 by mobile phase 2 that can easily be used in an atmospheric ion source. Such an ion source could be electrospray (ESI) ionization, or atmospheric pressure chemical ionization (APCI), among others.

FIG. 1B illustrates an embodiment similar to the embodiment shown if FIG. 1A. However, in FIG. 1B two voltages are applied; voltage V1 is applied to the steel tube 12 and thus mobile phase 1, while voltage V2 is applied to mobile phase 2. The voltage differential may be used in certain circumstances to improve transfer rates through the membrane 10 in either direction depending on the polarity of the applied potential and charge on the molecular species. Such an embodiment could be used to improve the ESI signal by purifying molecules in mobile phase 2 by removing contaminants through an appropriate membrane material into mobile phase 1 or by concentrating analyte molecules into mobile phase 2 from mobile phase 1. The voltage differential may be provided by any suitable means 21 such as a battery, power supply, multi-tap transformer or other power source, and maybe either AC or DC.

Figure 2:
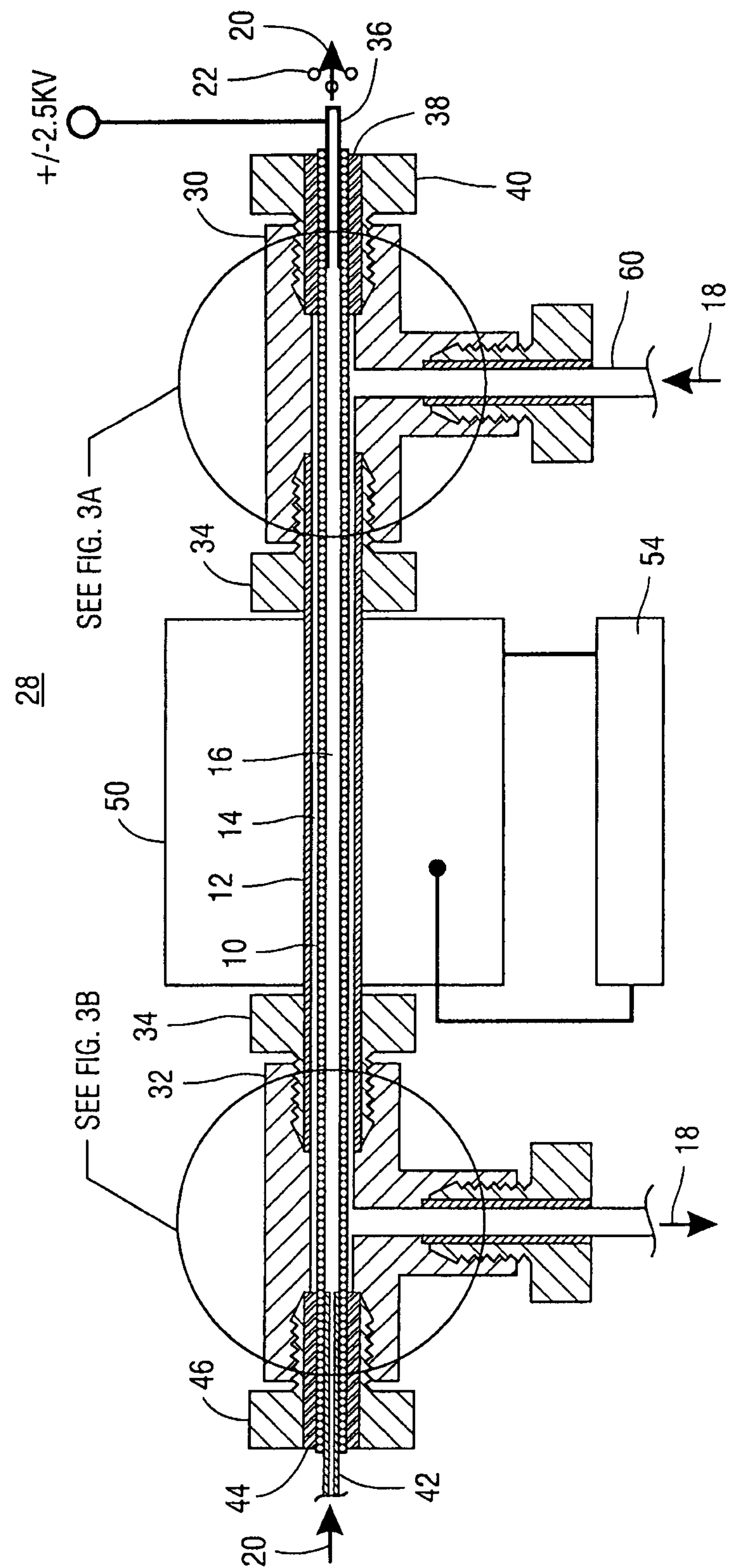
FIG. 2 illustrates an embodiment of a probe of the present disclosure using the tubular capillary membrane fitted within a stainless steel tube as shown in FIG 1A, but including an electrospray needle.
Figure 3A:
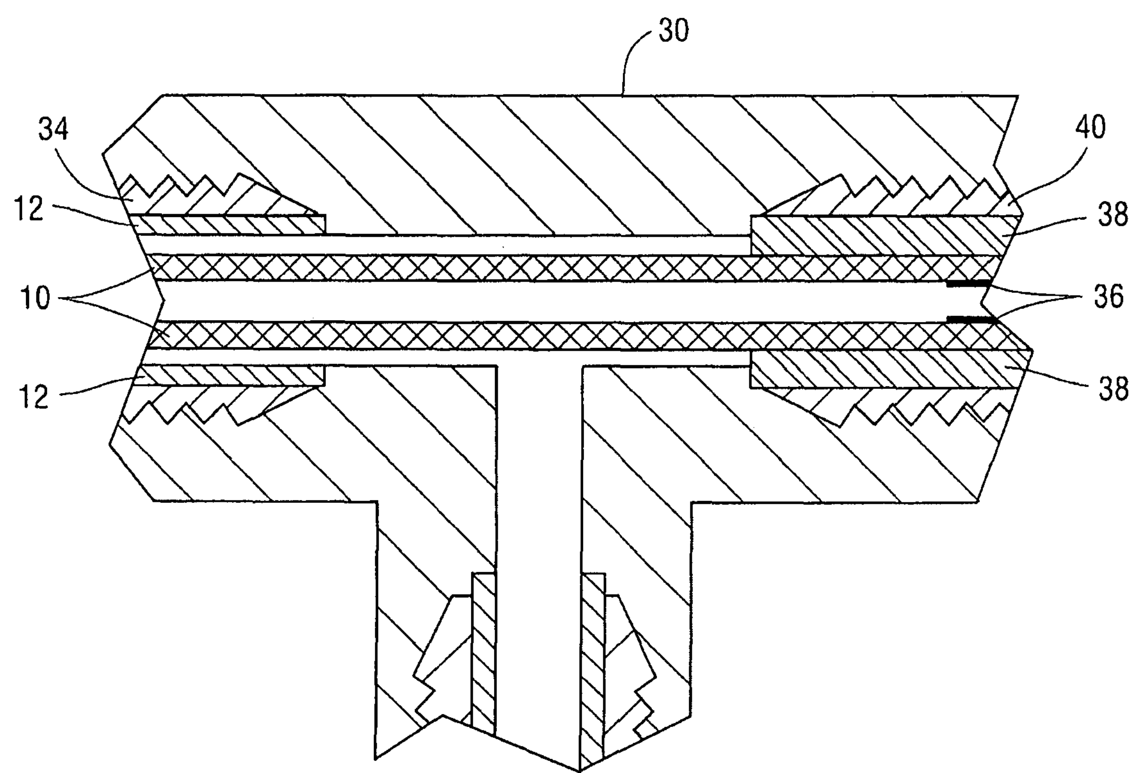
FIGS. 3A and 3B illustrate the right and left Tees of the probe of FIG. 2, respectively.
Figure 3B:
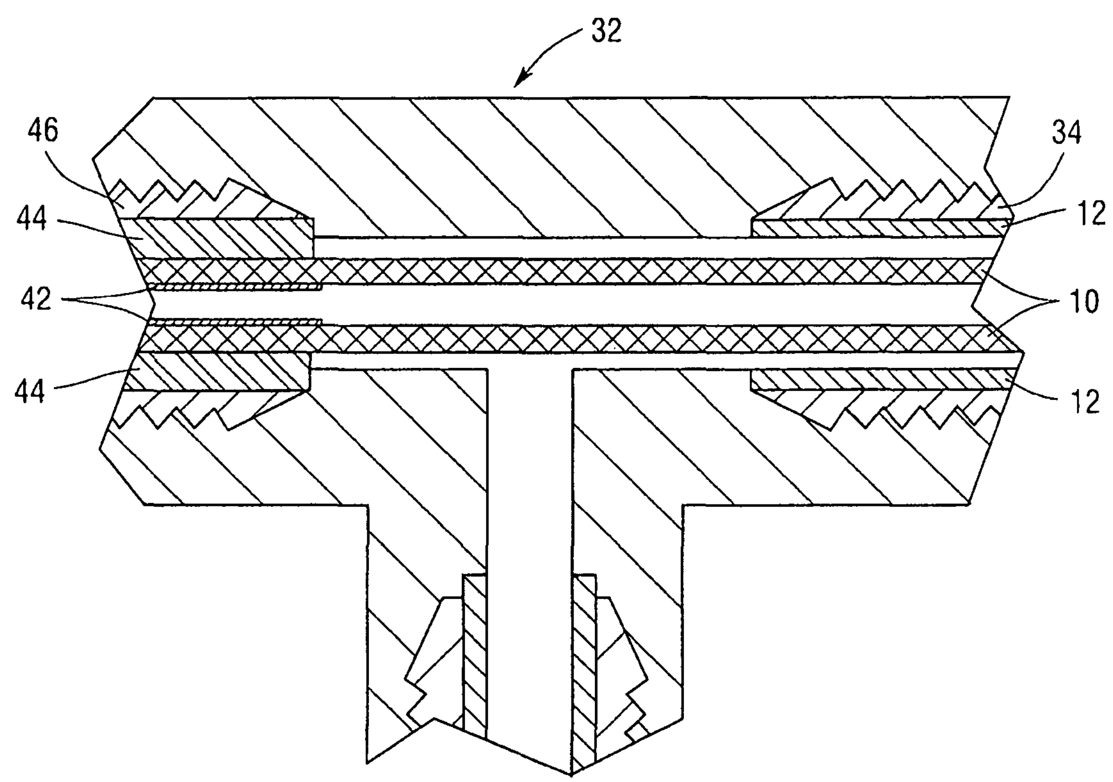

One version of a membrane probe 28 constructed according to the present disclosure is shown in FIGS. 2, 3A and 3B. The concept of the ESI membrane probe 28 was based on five main design considerations: i.) electrospray ionization rather than the more traditional EI/CI, although such other ionization techniques may be used ii.) two liquid mobile phases separated by the membrane rather than a liquid and gas phase, iii.) a capillary PDMS membrane, iv.) a short transfer line and v.) membrane heating. Design criteria four required the ESI needle to be incorporated into the membrane thus eliminating a transfer line and the fifth criteria of heating should improve the analyte permeation rate and thus signal strengths.

The membrane probe 28 uses, for example, a tubular, PDMS capillary membrane 10 with dimensions of, for example, 0.025" o.d. by 0.012" i.d. and approximately 12 cm long. The capillary membrane 10 is inserted into a stainless steel tube 14 with dimensions of, for example, 0.0625" o.d. by 0.040" i.d. and approximately 10 cm long. The right end of the membrane 10 and steel tube 12 are inserted into a right Tee 30 (See FIG. 3A) while the left end of the membrane 10 and the steel tube 12 are inserted into a left Tee 32 (See FIG. 3A). The Tees 30 and 32 may have, for example, a bore having an i.d. of 0.0625". The stainless steel tube 12 butts into each Tee 30, 32 and a seal is made with a standard HPLC PEEK fitting and 1/16" ferrules 34.

A steel electrospray needle 36 (e.g. 28 G) with an outside dimension greater than 0.012" (to allow for a good seal) is inserted into the membrane 10 at the extreme right side of the probe 28, thus integrating the membrane 10 and the needle 36. By "integrating" it is meant that the needle 36 forms a part of the mobile phase 2 flow path with little or no intervening mobile phase 2 flow path between the membrane 10 and needle 36. The mobile phase 2 is immediately ionized at the needle's tip and is directly transferred to an ionization region 22 of a mass spectrometer. Burrs on the ends of the needle 36 were removed by dipping in an aqua-rega solution for approximately 1 minute and then immediately washing with water. The end of the membrane 10 carrying the needle 36 is inserted into a Teflon tube 38 (e.g. 0.625" o.d.×0.030" i.d.) that acts as a sleeve. A ferrule 40 seals the Teflon tube 38 to the membrane 10, and the membrane 10 to the needle 36. At the other end of the probe 28, a capillary 42 such as a fused silica capillary coated with polyimide, is inserted into the membrane 10, and this assembly is further inserted into a Teflon tube 44 (e.g. 0.625" o.d.×0.030" i.d.). A ferrule 46 seals the Teflon tube 44 to the membrane 10, and the membrane 10 to the capillary 42.

Heat can be provided to the membrane 10 by adding a thermal mass 50, such as a copper or aluminum heating block, around the exterior of the stainless steel tube 12. A thermocouple 52 may be inserted into a hole drilled into one end of the thermal mass 50 block and the thermal mass 50 may be wrapped with heating tape (not shown) and driven by a standard temperature controller 54 to maintain the thermal mass 50 to ±1 degree Celsius.

While the mobile phase 2 inside the capillary membrane flows to the right in FIG. 2 where the needle 36 is attached, the mobile phase 1 flows in the opposite direction. This flow arrangement maximizes the concentration of the analyte from mobile phase 1 to mobile phase 2. Additionally, the geometry of the capillary membrane 10 is also advantageous because it provides a means of concentrating the analyte by adsorption on a large surface area, (the outside of the membrane) followed by desorption from a surface area half that size, (the inner surface of the capillary membrane).

Preliminary tests were performed using the probe 28 of FIG. 2. Samples were injected into a flow of water (or other solvent) using a standard 6-port injector and these sample plugs entered a Tee port 60 on the right Tee 30 that directed the water flow to the space 14 between the outside diameter of the membrane 10 and the inside diameter of the tube 12. The analyte permeates from the outside to the inside of the capillary membrane 10 and is thus concentrated due to the geometry of the membrane 10. The analyte is desorbed from the inner surface of the capillary member 10 where it enters the mobile phase 2, i.e. a stream of methanol, ethanol, isopropanol or other suitable solvent for electrospray. An acid such as acetic or formic or other suitable acid can be added to mobile phase 2 to help with ESI and to charge the analyte so that it is less likely to permeated back through the membrane 10. In addition, cations such as $Li^+$ or $Na^+$ or $Ag^+$ can be added to mobile phase 2 to allow for enhanced ionization of molecules that do not typically ionize by proton addition. For negative ESI a suitable mobile phase without acid may be used.

Figure 4:
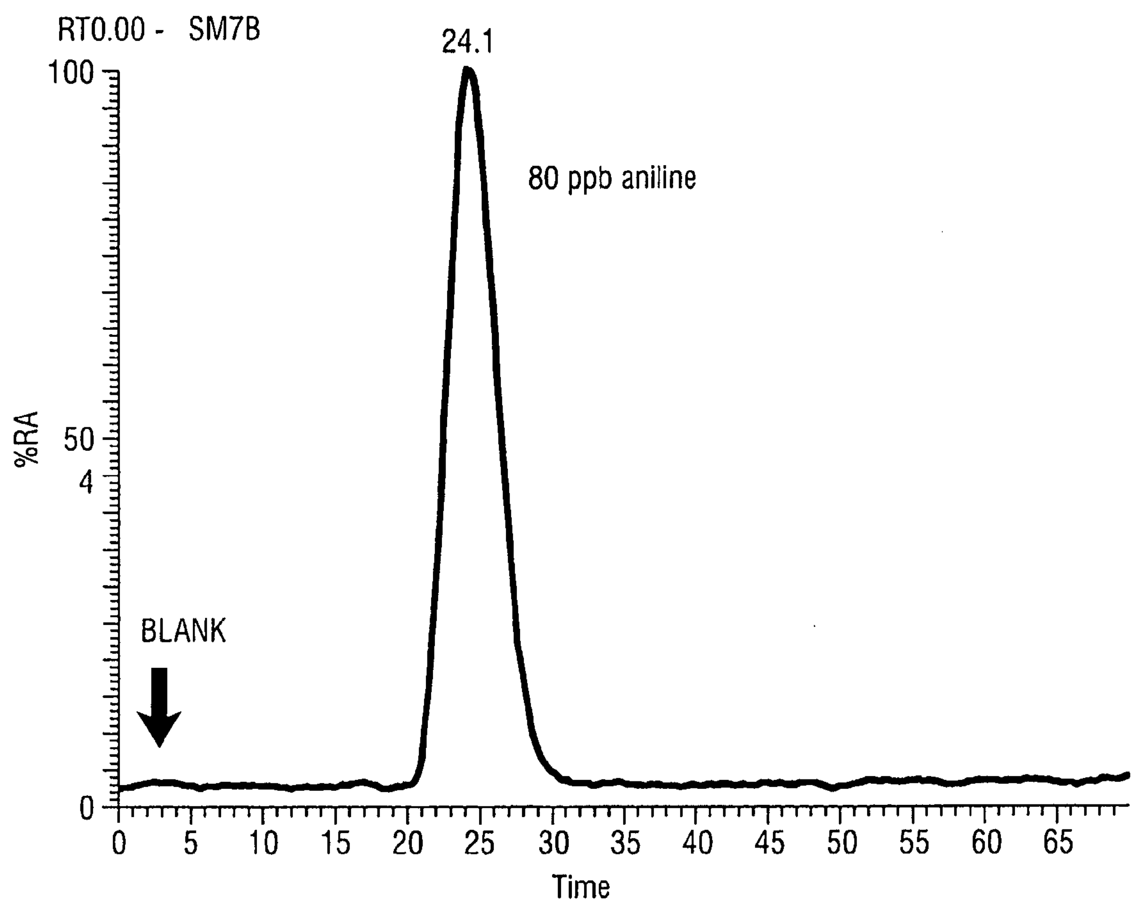
FIG. 4 illustrates a plot (using a probe constructed according to the teachings of the present disclosure) of ion current of m/z 9.1, 7 from aniline; at 1 minute an injection of HPLC grade water was made as a blank followed at 20 minutes by an injection of 1 μM (~80 ppb) aniline solution; other parameters: 100 μL sample loop, 7 point smooth, 5 μL/min methanol flow rate, 100 μL/min water flow rate, 2.5 KV on spray needle.

Preliminary results from the use of the probe the MIMS probe 28 are shown by a plot of ion current of m/z 9.1, 7 from aniline in FIG. 4. At 1 minute an injection of HPLC grade water was made as a blank followed at 20 minutes by an injection of 1 μM (~80 ppb) aniline solution. Other parameters used in the analysis include: 100 μL sample loop, 7 point smooth, 5 μL/min methanol flow rate, 100 μL/min water flow rate, and 2.5 KV was applied to the spray needle;

Additional tests were performed as follows. For mobile phase 1, a HPLC grade water was used and for mobile phase 2, HPLC grade methanol was used. When running in the positive ion mode, acetic acid was added to the methanol. Test samples of aniline, acetic acid and trifluoroacetic acid were from Sigma-Aldrich. Pyridine was from Fisher Scientific, and the environmental mixes of herbicides and phenols were purchased from Supelco (Bellefonte, Pa.).

The electrospray ion trap mass spectrometer used in this study was an LCQ model from Thermo Electron Corporation (San Jose, Calif.). The software used on the LCQ was Xcalibur version 1.1. The scan modes used were full scan MS, SIM, MS/MS and the 'turbo' scan. The turbo scan is a rapid scan used to increase sensitivity with reduced mass resolution. For comparison, some experiments used the standard LCQ electrospray ionization source. For all of the MIMS experiments, the standard LCQ ESI source was replaced with the MIMS probe which incorporated its own ESI source. The on-board valve of the LCQ mass spectrometer was used for flow-injection analysis (FIA).

To mount the probe assembly 28 to the mass spectrometer, the standard LCQ ESI probe head was removed and the MIMS probe 28 was positioned with the ESI needle 36 approximately 5-8 mm away from the LCQ heated capillary inlet.

Four operating parameters of the MIMS probe 28 were optimized using continuous flow experiments: electrospray voltage, internal mobile phase flow rate, external mobile phase flow rate and membrane temperature.

The MIMS probe 28 ESI needle 36 voltage was optimized using two separate methods. The stability of the Taylor cone and spray was viewed using an Olympus SZ-CTV 10-60X magnifying scope and the stability and signal strength of the mass spectrum was observed using the mass spectrometer. An ESI voltage of 2.5 kV was determined to be optimal. Higher voltages resulted in multiple Taylor spray cones and instability of the spray. The MIMS probe ESI voltage is less than the standard value used on the LCQ of 4-5 kV as expected given the smaller ESI needle dimensions used on our MIMS probe. No sheath gas was used to help with nebulization.

For the internal mobile phase (i.e. mobile phase 2) and the external mobile phase (e.g. mobile phase 1) flow rate and temperature optimization experiments, the external mobile phase, which is normally water, was replaced with 1 μM aniline and the intensity of the $[M+H]^+$ ion at m/z 94.1 averaged over 100 scans at each new setting was plotted versus the parameter of interest. The optimum setting was determined from the maximum signal recorded in these plots. To determine an optimal internal flow rate, the external flow rate was held at 60 or 100 μL/min while the probe was operated at 60°

Figure 5A:
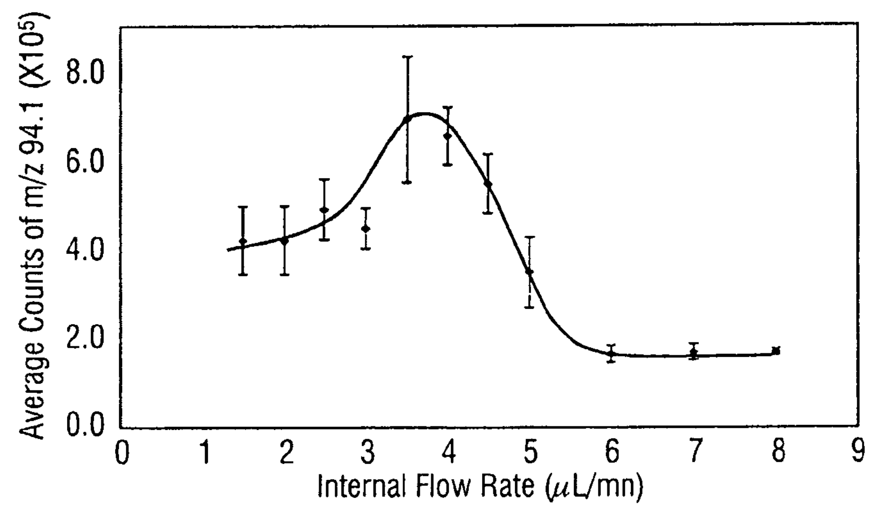
FIGS. 5A, 5B, and 5C illustrate test results used to determine operating parameters.

C. Each time the value of the internal flow rate was changed the probe was equilibrated for up to 10 minutes. The average counts for m/z 94.1 were plotted against the internal flow rate in FIG. 5A. From this plot, 3.5 μL/min was selected as a suitable flow rate for the internal solvent. The plot shows that the signal was optimized at flow rates between 2-4 μL/min. Because ESI is a concentration, rather than amount dependent technique, a reduced signal must be due to either reduced analyte concentration or some other factor. At higher internal flow rates, it is expected that less exposure time of the desorbing sample to the internal mobile phase would result in a smaller concentration of analyte in the internal solution, however, at the low flow rates, only higher analyte concentrations would be expected until equilibrium was reached. At the lowest internal flow rates studied, the reduced signal may be the result of a poor spray which can also occur with the standard LCQ ESI source at less than 3 μL/min. Further optimization of the ESI voltage may have improved the spray at these low flow rates, but we did not undertake these experiments.

The use of a two liquid interface where the internal flow rate may be reduced to allow the analyte more time to concentrate into the internal solvent is an advantage of our technique over the pervaporization techniques because in our liquid/membrane/liquid case, the analyte is not diluted by rapid gaseous diffusion. Gaseous diffusion in the pervaporization case would also be of concern in a flow injection analysis (FIA) experiment, however, with the ESI MIMS technique, the slow diffusion rates of analytes in the liquid prevent rapid dilution and limit peak broadening.

Figure 5B:
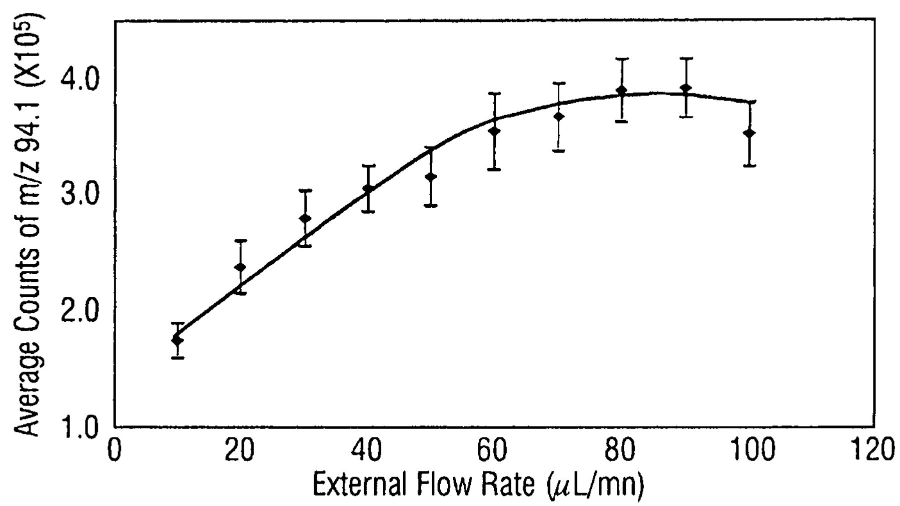

To determine the optimal external mobile phase flow rate we set the internal flow rate to 3.5 μL/min and heated the probe to 60° C. The external flow rate was varied, and each time the setting was changed the system was allowed to equilibrate. The average counts for m/z 94.1 were plotted against the external flow rate. From this plot it was determined that 60 μL/min was the optimal external flow rate as shown in FIG. 5B.

Figure 5C:
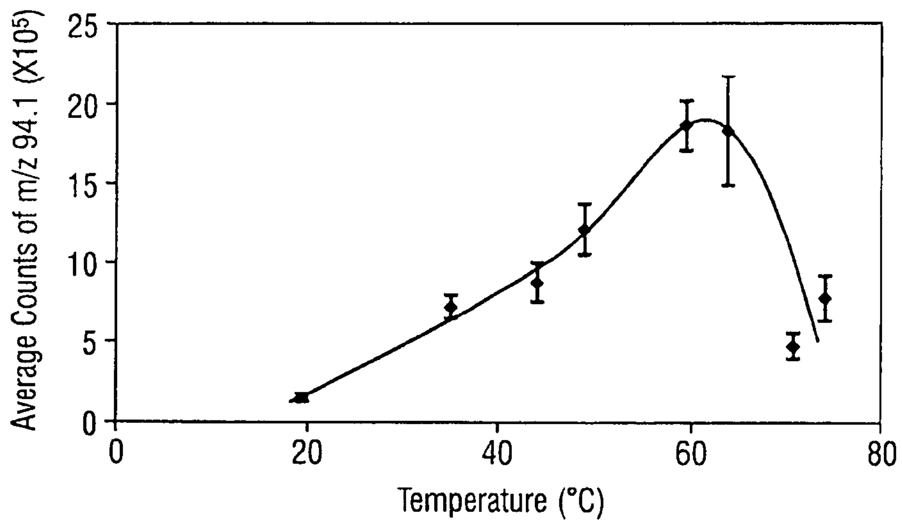

To determine the optimal membrane temperature, the internal and external flow rates were set to 3.5 μL/min and 60 μL/min, respectively, and the temperature was varied from 20 to 75° C. After each change in temperature the system was allowed to equilibrate for 10 minutes. The average counts for aniline at 94.1 m/z were plotted against membrane temperature as shown in FIG. 5C with the error bars representing the standard deviation of the 100 scans collected. From 20-60° C. there is an increase in signal until a maximum is reached at 60° C. This signal increase is due to improved analyte permeation through the membrane at higher temperatures. Above 65° C., the boiling point of methanol, the signal becomes erratic due to the formation of gas bubbles disrupting the liquid flow to the electrospray needle. By 70° C. the signal was reduced by four fold. Other solvent systems with higher boiling points should be explored in the ESI MIMS probe to further enhance the analyte flux at even higher temperatures. Ethanol (b.p. 78° C.) should allow for a higher operating temperature and improve analyte permeation. Previous MIMS pervaporization experiments with liquid water showed an improved ion signal for 120 ppm benzene up to approximately 95° C. It should be noted that the entire length of membrane would not have been heated to 60° C. since the ends of the membrane, approximately 1 cm in length were not heated well.

Flow injection analysis (FIA) experiments were used so that a sample plug could be injected inbetween segments of pure water. By using FIA we could flush the membrane with clean solvent between injections and also use background subtraction to reduce the chemical noise for our analysis. To obtain low detection limits we wanted to maximize the period for which the sample was exposed to the membrane; therefore a sample loop size was selected to allow for this maximal rise. A sample of 1 μM aniline was injected three times, with a different sample loop size each time. When the sample loop was increased from 100 μL to 250 μL we saw an increase in the peak height and area by a factor of about 2.5. However, when we went from a 250 μL loop to a 500 μL sample loop the peak broadened with no significant change to the signal height. To reduce the time for analysis we selected a 250 μL volume and that sample loop was used for all experiments. An external flow rate of 60 μL/min allows for a three min analyte exposure time.

Admittedly, our determination of the optimum parameters was not exhaustively iterative and we also did not change design parameters such as the membrane length or wall thickness or perform extensive studies with other internal solvent systems. This methodology was used to reach reasonably good settings so as to efficiently explore the potential of the ESI MIMS probe as a useful analytical device. Further studies should improve the performance of the ESI MIMS probe.

To demonstrate the performance of the probe, a figure of merit is shown in FIGS. 6A and 6B where we compare the improved signal intensity in the mass chromatogram of 1 ppm aniline in water, m/z 94.1, using the ESI MIMS probe 28 compared to the LCQ standard ESI source with no membrane. Three notable features are seen in this data. One, the signal is approximately 10× higher due to the enrichment of aniline in the methanol with the MIMS probe; two, the noise level is improved by approximately 7× which we expect is primarily due to the improve ESI performance by electrospraying methanol instead of 100% water; and finally, the width of the peak using ESI MIMS is about 20% greater and has significantly more tailing due to the permeation of the aniline through the membrane and the residue bleed from the PDMS membrane. The overall S/N improvement of the ESI MIMS method was 70× over direct ESI of a sample in water.

The linear dynamic range was tested for aniline and pyridine, and it was determined that the linear dynamic range for aniline was from 100 pptr to 600 ppb and for pyridine it was 1 ppb to 600 ppb. Above this range the MIMS system was not quantitatively accurate. The drop off in signal may be due to the membrane nearing saturation and so the signal will no longer increase in the same proportion to concentration. The influence of ionization efficiency for a specific analyte may also change as the analyte composition changes and this effect should be explored at the concentration levels of interest for quantitative analysis work.

The detection limits of the ESI MIMS probe were tested for four main classes of compounds: organic acids, organic bases, herbicides, and phenolic compounds. For these measurements the mass spectrometer was operated in SIM mode with a mass isolation width of ±2.5 Da. The detection limits for compounds in each of these classifications are shown in Table 1.

TABLE 1

Detection limits using the ESI MIMS probe and SIM scan mode.

| | Molecular Formula | Ion (m/z) | Limit of Detection | S/N |
|---|---|---|---|---|
| Positive Ions<br>Organic Bases | | | | |
| Aniline | $C_6H_7N$ | 94.1 | 75 pptr | 8 |

TABLE 1-continued

Detection limits using the ESI MIMS probe and SIM scan mode.

| | Molecular Formula | Ion (m/z) | Limit of Detection | S/N |
|---|---|---|---|---|
| Pyridine | $C_5H_5N$ | 80.1 | 1.0 ppb | 14 |
| Herbicides | | | | |
| Alachlor | $C_{14}H_{20}ClNO_2$ | 269.9 | 5.0 ppb | 94 |
| Atrazine | $C_8H_{14}ClN_5$ | 216.1 | 250 pptr | 22 |
| Butachlor | $C_{17}H_{26}ClNO_2$ | 311.9 | 1.0 ppb | 24 |
| Metolachlor | $C_{15}H_{22}ClNO_2$ | 283.9 | 1.0 ppb | 59 |
| Simazine | $C_7H_{12}ClN_5$ | 202.0 | 500 pptr | 24 |
| Negative Ions | | | | |
| Organic Acids | | | | |
| Acetic Acid | $C_2H_4O_2$ | 59.0 | 1.1 ppm | 16 |
| Trifluoroacetic Acid | $C_2HF_3O_2$ | 113.0 | 150 ppm | 64 |
| Phenolic Compounds | | | | |
| 2,4-Dinitrophenol | $C_6H_4N_2O_5$ | 183.0 | 1.5 ppm | 41 |
| 4-Chloro-3-methylphenol | $C_7H_7ClO$ | 141.0 | 500 pptr | 50 |
| Pentachlorophenol | $C_6HCl_5O$ | 265.0 | 100 pptr | 10 |

The detection limits are in the low ppb to high pptr range, with the exception of acetic acid, trifluoroacetic acid, and 2,4-dinitrophenol, all of which have detection limits in the ppm range. These acids have higher detection limits because a significant proportion of these molecules are dissociated in the external aqueous phase and so ion permeation through the nonpolar membrane should be poor. Trifluoroacetic acid (TFA) is a much stronger acid than acetic acid and its detection limit is two orders of magnitude higher, indicative that a much higher proportion of the TFA molecules are dissociated in the aqueous sample. Although 2,4-dinitrophenol is not significantly dissociated in water, the nitro groups are quite polar, and a lower permeation rate through the membrane is expected.

To determine the amount of analyte that the probe extracts from the sample the quantitative properties of the probe were utilized. Aniline solutions of 0.1 μM, 0.5 μM, 1 μM, 1.5 μM, and 2 μM were run and the average peak area over three injections were plotted against the concentration of aniline in the solution to determine a calibration curve. Next, three injections of an aniline solution of 10 μM were made during which time the waste eluting from the probe was collected. The total volume infused was 3.00 mL. This waste solution was re-injected three times and the calibration curve was used to determine that the waste had a concentration of 1.5 μM aniline. The three injections of 10 μM aniline totaled 750 μL sample equal to $7.50\times10^{-3}$ μmoles. The 3.00 mL of 1.5 μM aniline waste equaled $4.5\times10^{-3}$ moles. This indicates that $3.00\times10^{-3}$ μmoles or 40% of the analyte molecules permeated the membrane. If we consider the small total volume of 175 μL of the internal mobile phase, methanol, used during the 50 minute experiment compared to the volume of external water used, we see that the probe does act as a good concentrator. During the experiment, the average concentration of aniline in the external solvent was 2.5 μM and the average internal concentration of aniline was 17.14 μM or 6.86 times higher.

Figure 7:
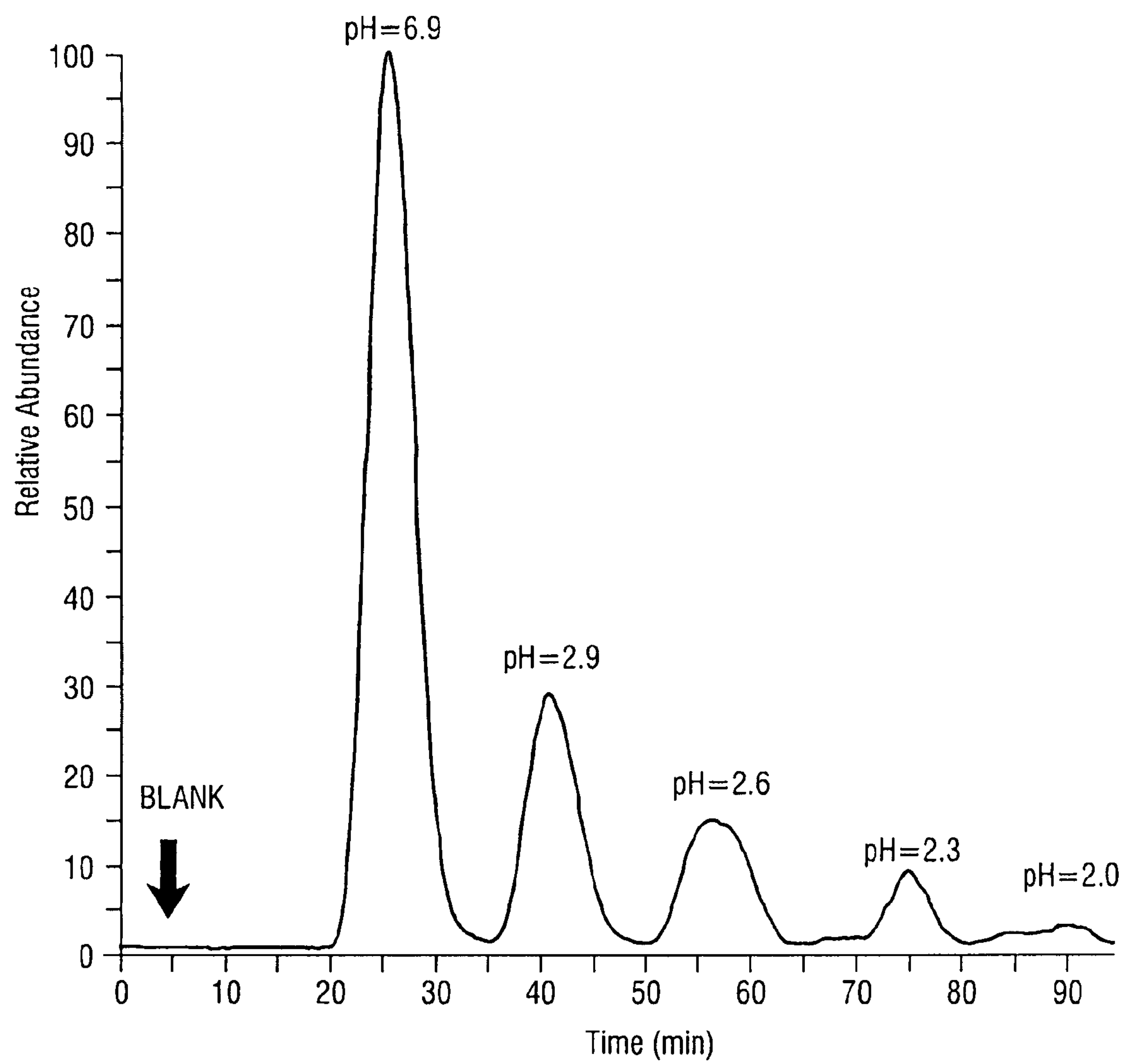
FIG. 7 is a plot demonstrating how the permeation of 1 μM aniline samples through the membrane at different pH values can be used to change the concentration of an analyte in the internal mobile phase.

Additives in either the external or internal mobile phase can be used to improve permeability and/or the ionization efficiency of the analytes. FIG. 7 shows how the pH of the aqueous sample can be adjusted with HCl to either enhance or suppress the permeation of aniline. A blank was injected at 5 minutes and samples of 1 μM aniline, at different pH values of 6.9, 2.9, 2.6, 2.3, and 2.0 were injected at every additional 15 minutes. At low pH a higher proportion of aniline would be protonated, which would inhibit permeation through the membrane. We still see a significant peak below the pKa=4.63, which is probably partially due to mixing of the sample plug with the external mobile phase, which would occur in the Tees. Although the internal mobile phase encounters negligible dead volume inside the device, the external mobile phase flows through a 90 degree bend through the tee and this is a site where mixing would occur. Future ESI MIMS probe designs should attempt to overcome this mixing region.

Figure 8:
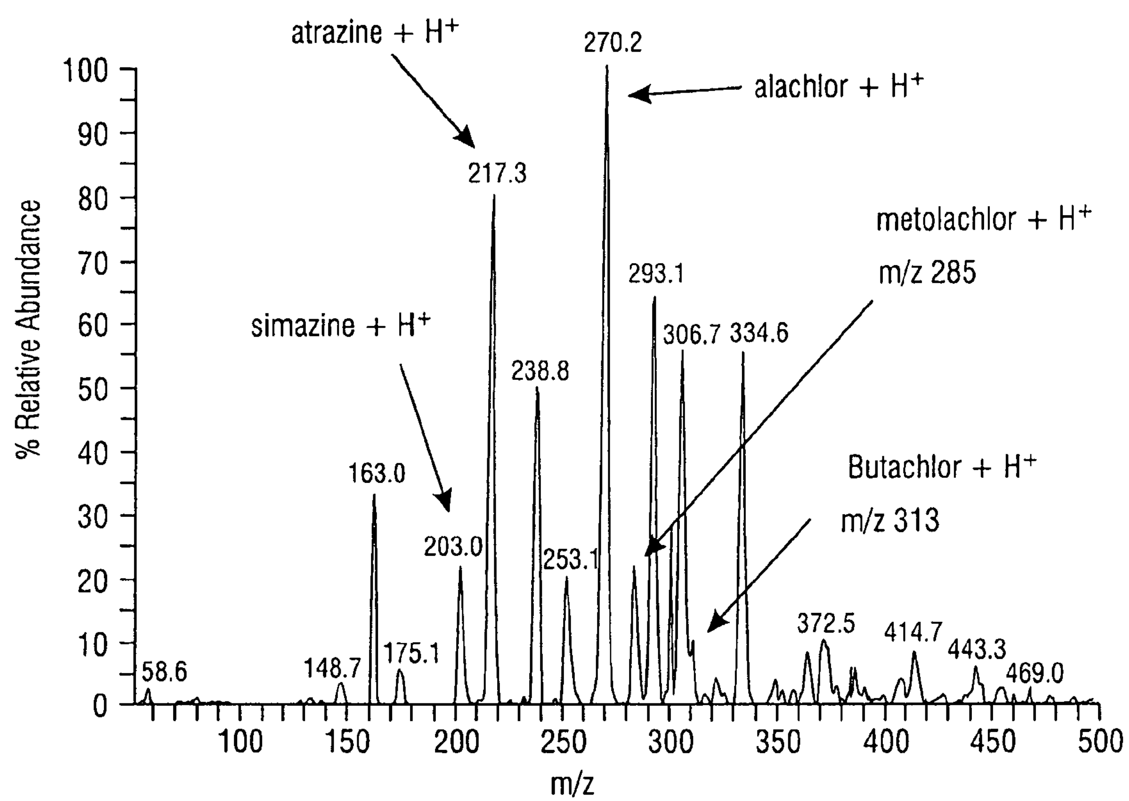
FIG. 8 illustrates a survey scan of a mixture of a five herbicide mixture each at 100 ppb with background subtraction using the ESI MIMS probe of the present disclosure and a rapid scanning technique.

Increasing the RF ramp during analysis is a rapid scan feature of the LCQ called a "Turbo scan". This scan allows trapped ions to be scanned out of the trap much more quickly than in the normal scan rate. This scan significantly decreases the mass resolution, but it increases the signal height and in several cases can allow for determinations that were not possible in the full scan mode. The capabilities of the Turbo scan were demonstrated for the molecular weight determination of a protein. A mixture of five herbicides (alachlor, atrazine, butachlor, metolachlor, and simazine) each at a concentration of 100 ppb where injected. In the Turbo scan mode shown in FIG. 8, all five herbicides are observed. This MIMS example shows the advantage of first using the rapid scan for a survey analysis which could be followed by a mass spectrometry/mass spectrometry (MS/MS) scan of each analyte for identification.

Figure 9:
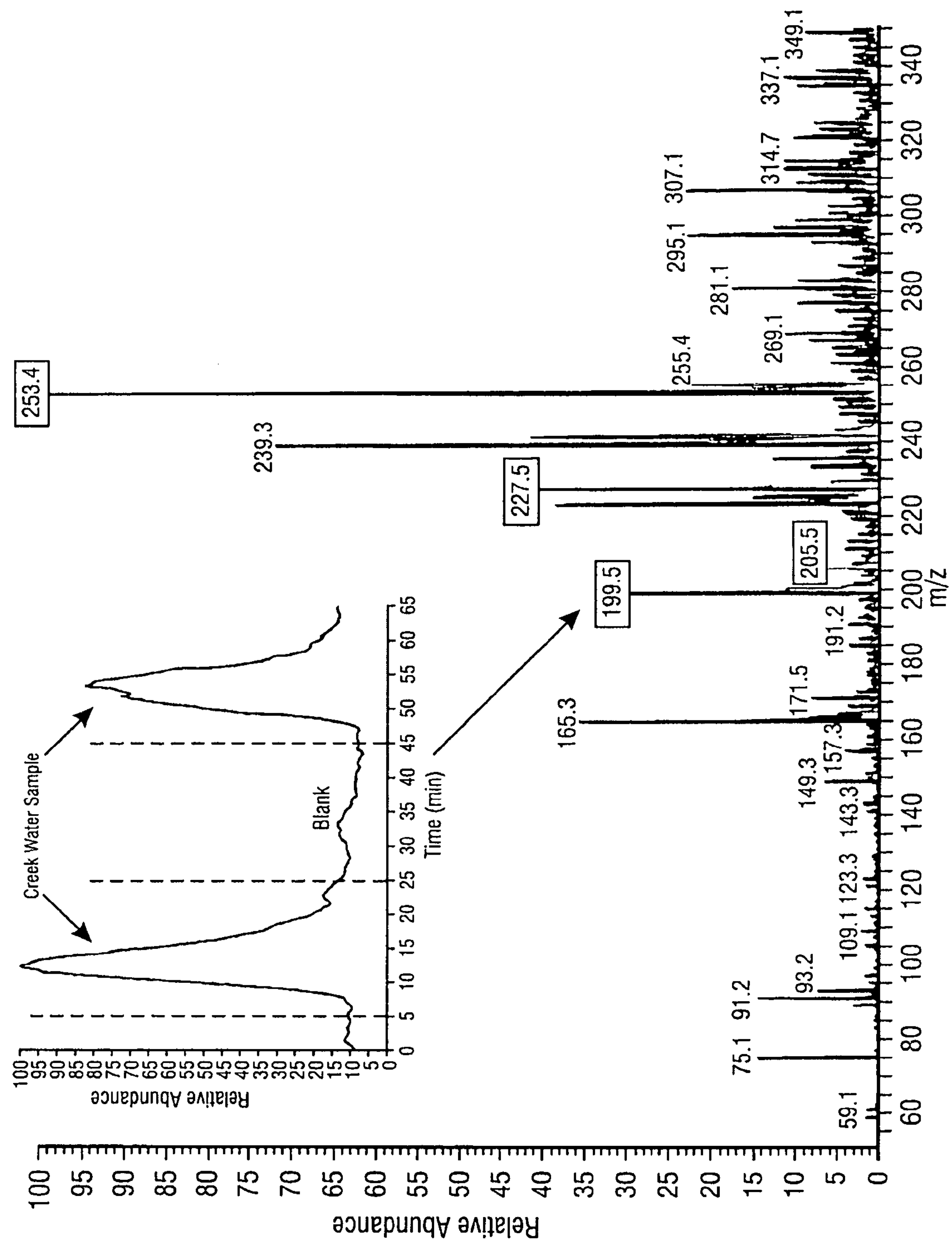
FIG. 9 is a mass spectrum from an analysis performed according to the teachings of the present disclosure showing the presence of four contaminants (boxed mass assignments) found in Buffalo Creek (Freeport, Pa.) water in negative ion mode.

For a real life application of the MIMS ESI probe, a water sample was taken from the water treatment plant on Buffalo Creek a few miles upstream from Freeport, Pa. The 50 mL sample was collected from a pipe carrying the treated effluent that flowed into the creek. The sample was filtered with a 0.2 micron filter to remove any organic material that could dirty the membrane, injected into the MIMS probe and the permeate was electrosprayed in negative ion mode. As shown in FIG. 9, contaminant ions with masses shown in boxes were detected at m/z 199.5, 205.5, 227.5, and 253.4. The FIA mass chromatogram of one of the contaminants is shown in the inset where an injection of a blank between two injections of the effluent shows the presences of the molecule at m/z 199.5. Although not identified, the observation of the four contaminants shows the utility of the ESI MIMS probe for environmental analysis.

According to another embodiment of the present invention, mobile phase 1 may be a gas. Volatile organics in the gas phase are adsorbed onto and permeate through the membrane and are removed at the other side by a liquid mobile phase that can easily be used in an atmospheric ion source. Examples are shown in FIGS. 10-13.

Figure 10:
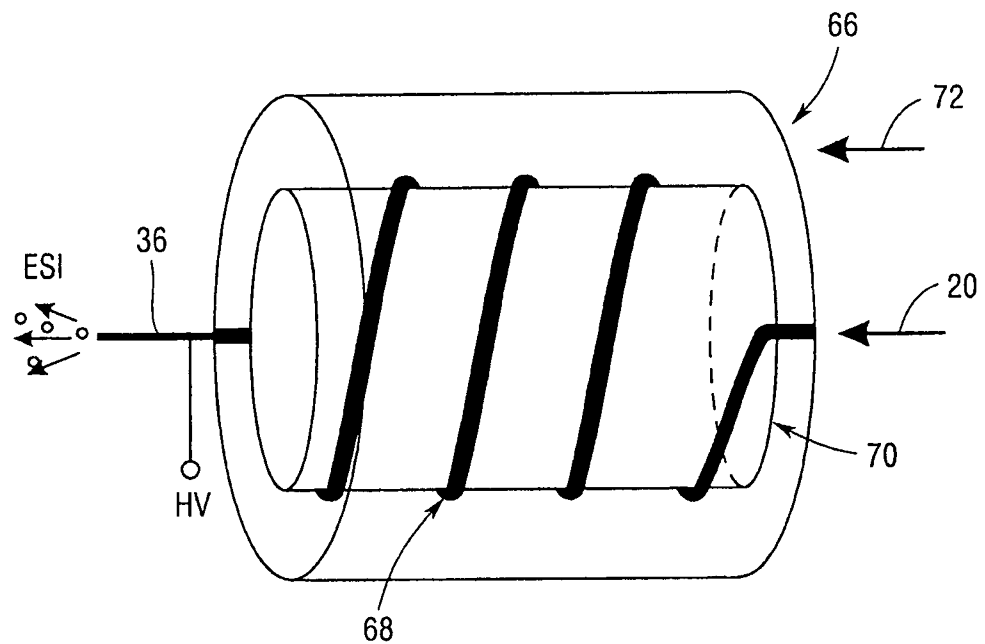
FIG. 10 illustrates another embodiment of the probe of the present disclosure in which a helical capillary membrane is supported by a wire frame for air analysis.

Turning first to FIG. 10, an air membrane probe 66 is illustrated. The probe 66 is comprised of a capillary membrane 68 wound about a wire support frame 70 and having an integrated needle 36. A gaseous mobile phase 1 is introduced into the probe 66 as shown by the arrow 72 while the liquid mobile phase 2 flows through the capillary membrane 68 as shown by the arrow 20. The probe 66 can be temperature controlled so as to be cooler or warmer than ambient.

Figure 11:
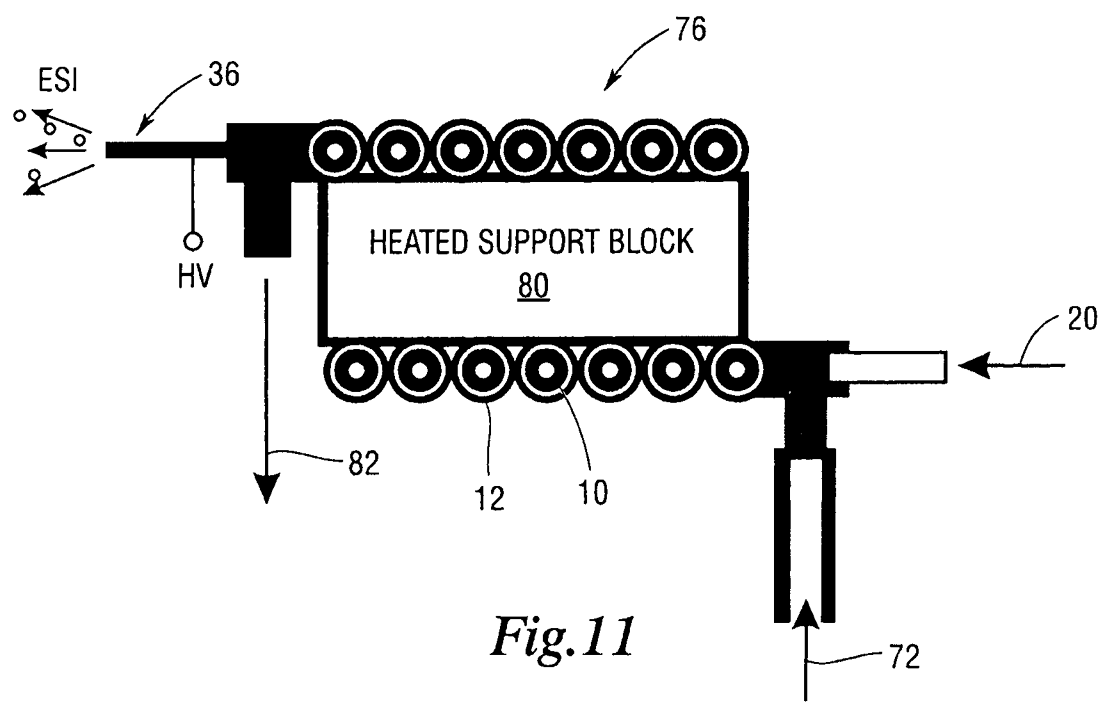
FIG. 11 is a cross-section view of another embodiment of the probe of the present disclosure in which a capillary membrane is positioned inside a stainless steel tube, and a gas is forced through the probe for the analysis.

FIG. 11 is a cross-sectional view of another air membrane probe 76 that uses ESI. The probe 76 is similar to the probe 28 of FIG. 2A except that the stainless steel tube 12 carrying the membrane 10 is wound about a heated support block 80. Another difference is that mobile phase 1 is a gas as shown by the arrow 72. A third difference is the use of a vacuum pump (not shown) which pulls a vacuum (e.g. 100-10,000 mL/min) as represented by the arrow 82 for the purpose of pulling the gaseous mobile phase 1 through the probe 76.

Figure 12:
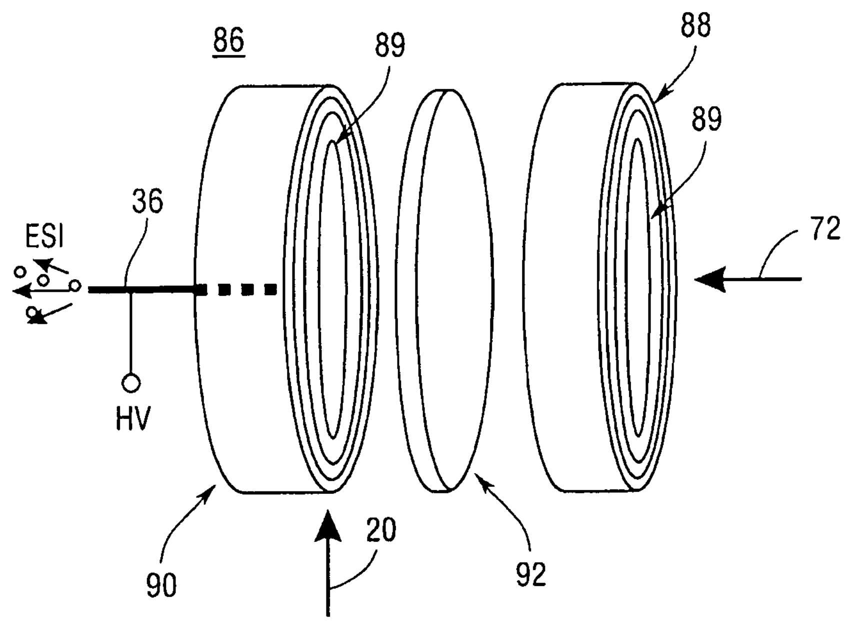
FIG. 12 is an exploded view of another embodiment of the probe of the present disclosure which illustrates a spiral membrane air probe.

FIG. 12 is an exploded view illustrating another embodiment of an air membrane probe 86. The probe 86 is comprised of a cover plate 88 having a spiral geometry 89 formed therein. The membrane is further comprised of a support member 90 having the same spiral geometry 89 formed therein. The spiral geometry shown in FIG. 12 is one of many possible geometries. A sheet membrane 92 is sandwiched between the cover plate 88 and the support member 90 so that the sheet membrane 92 forms one of the walls of the flow path for mobile 2. An integrated needle 36 is also provided. In this case, there is small gap between the wall formed by the sheet membrane 92 and the needle. The gaseous mobile phase 1 is represented by the arrow 72 while the liquid mobile phase 2 is represented by the arrow 20 as in the other figures.

Figure 13:
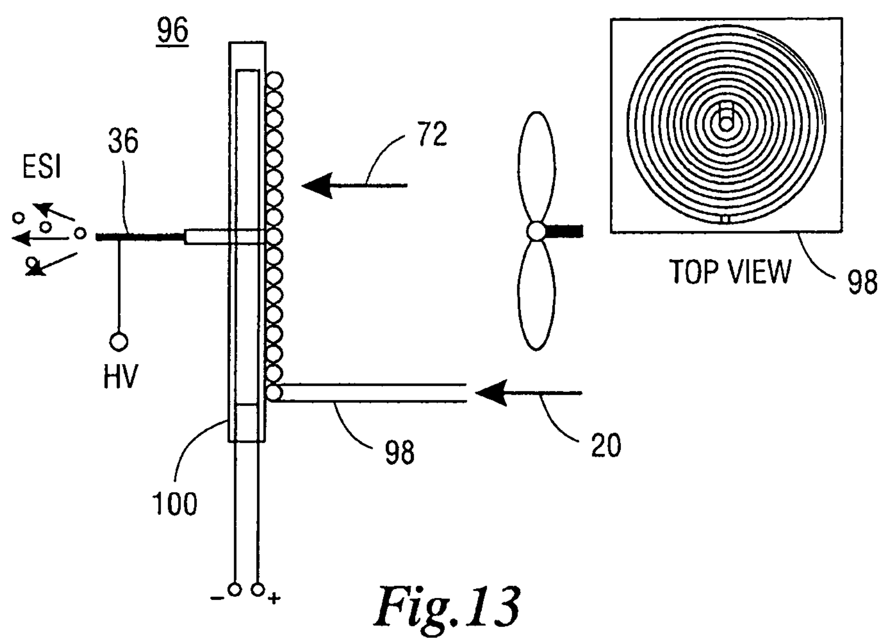
FIG. 13 illustrates yet another embodiment of an air membrane probe according to the teachings of the present disclosure having a Peltier heating/cooling device.

FIG. 13 illustrates another embodiment of an air membrane probe 96 having a Peltier heating/cooling device 100. In FIG. 13, a membrane 98 is spiral wound (see top view) on one surface of the Peltier device 100. The capillary membrane is cooled to condense out volatile organics onto the membrane surface; the membrane can then be heated to rapidly transfer the adsorbed analyte through the membrane into the internal mobile phase (i.e. mobile phase 2). This cooling and heating technique could also be used in a liquid/membrane/liquid configuration to improve analyte signal.

Figure 14:
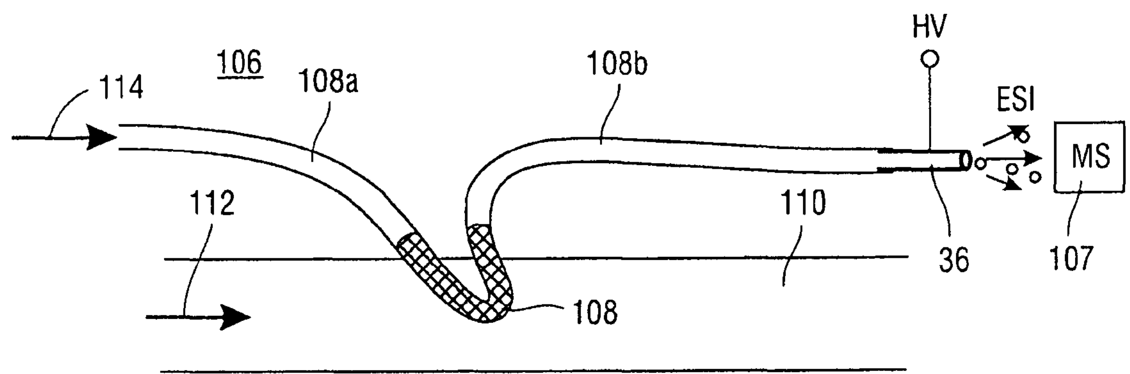
FIG. 14 illustrates how the teachings of the present disclosure may be used to monitor molecules in vivo using a capillary membrane probe coupled to an electrospray ionization mass spectrometer.

FIG. 14 illustrates how the teachings of the present disclosure may be used to monitor molecules in vivo using a capillary membrane probe 106 coupled to an electrospray ionization mass spectrometer 107. The probe is comprised of a tubular capillary membrane 108 attached on either end by non membrane tubes 108*a*, 108*b*. The capillary membrane is inserted into a blood vessel 110 or other location in a living body. Mobile phase 1 is the fluid flowing in the living body as represented by the arrow 112 while mobile phase 2 is represented by the arrow 114.

Figure 15:
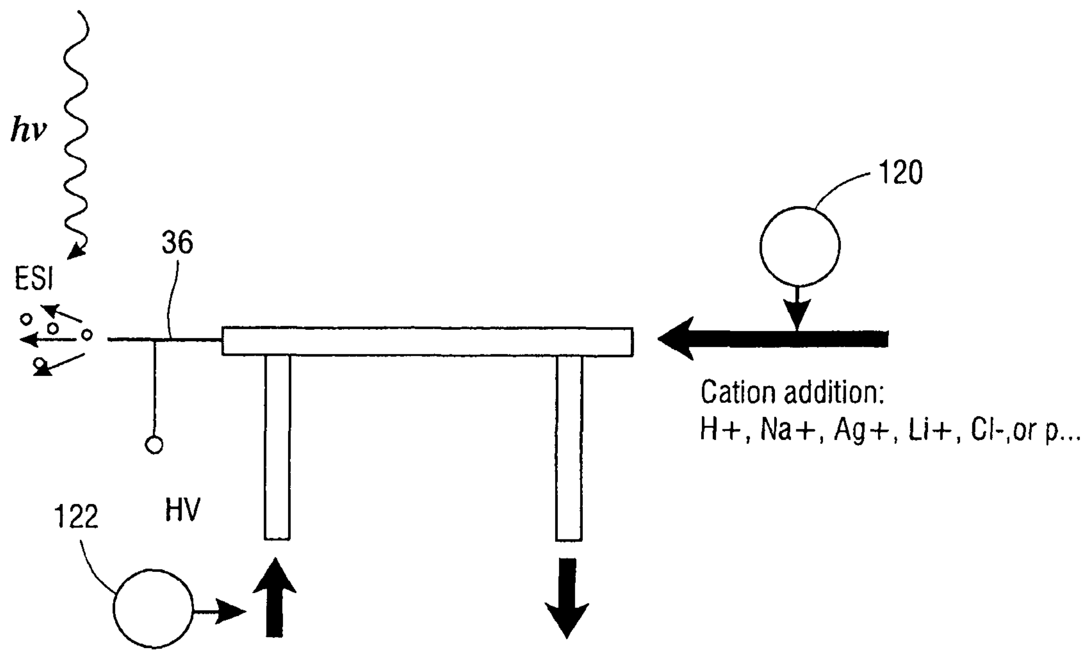
FIG. 15 illustrates a probe constructed according to the teachings of the present invention having an adduct addition or photoionization.

FIG. 15 illustrates a probe constructed according to the teachings of the present invention. A first means 120 for inserting additives into mobile phase 1 and a second means 122 for inserting additives into mobile phase 2 are illustrated. The means may be any suitable device (e.g. syringe, pump, among others) suitable for inserting the additive into the mobile phase. FIG. 15 illustrates the addition of various cations (e.g. H+, Na+, Ag+, Li+, $Cl^-$, K+, among others) into mobile phase 2. Various different means of ionization may be used with the probe of the present disclosure including, electrospray ionization (ESI), atmospheric pressure chemical ionization (APCI), atmospheric pressure photo-ioization (APPI), inductively coupled plasma (ICP), among others.

Figure 16A:
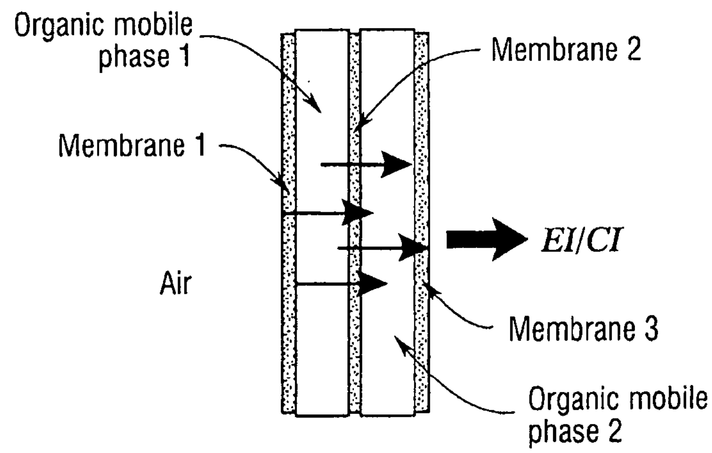
Figure 16B:
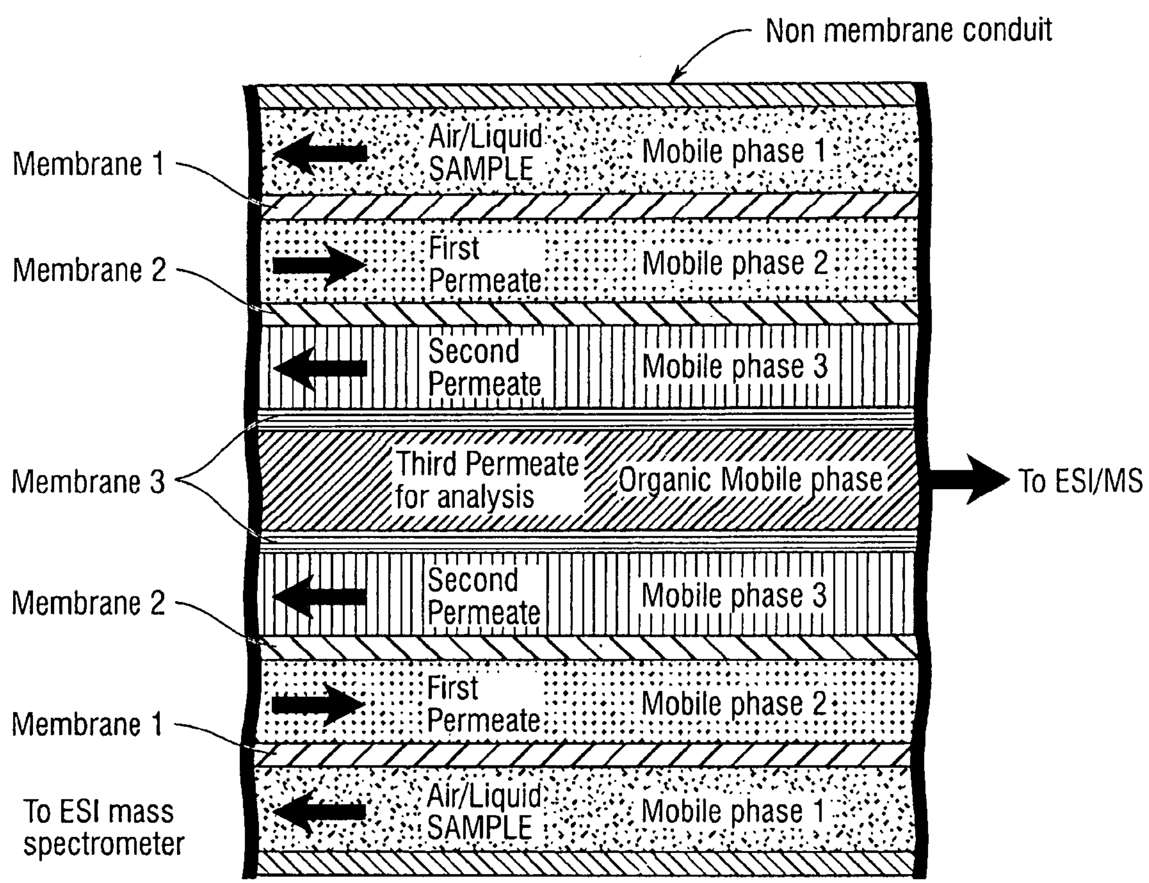

FIGS. 16A and 16B illustrate embodiments according to the teachings of the present invention using multiple membranes with an ESI source. In FIG. 16A the gaseous analyte molecules are adsorbed onto the surface of membrane 1 and are transferred into the mobile phase 1. A second step of analyte transfer occurs through membrane 2 and into the mobile phase 2. The analyte pervaporates from membrane 3 and undergoes electron ionization (EI) or chemical ionization (CI). In FIG. 16B we show FIA with three concentric membranes. The analyte is purified in stages from the sample plug through the membrane 1 and into mobile phase 2, and then from mobile phase 2 through the second membrane into the mobile phase 3. From mobile phase 3, the analyte passes through membrane 3 and into an organic mobile phase. Once in the organic mobile phase, the liquid solution goes under ESI. These embodiments can be used for additional stages of purification or selectivity if different membranes are used.

Figure 17A:
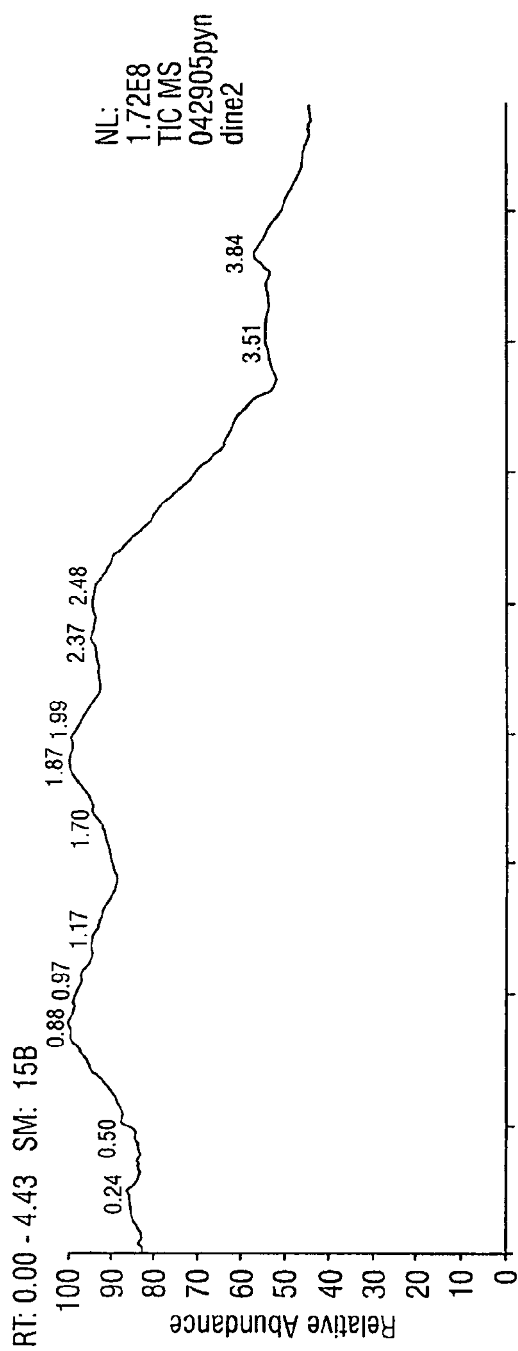
FIGS. 17A and 17B illustrate results from using a MIMS probe constructed according to the teachings of the present invention for sampling air.
Figure 17B:
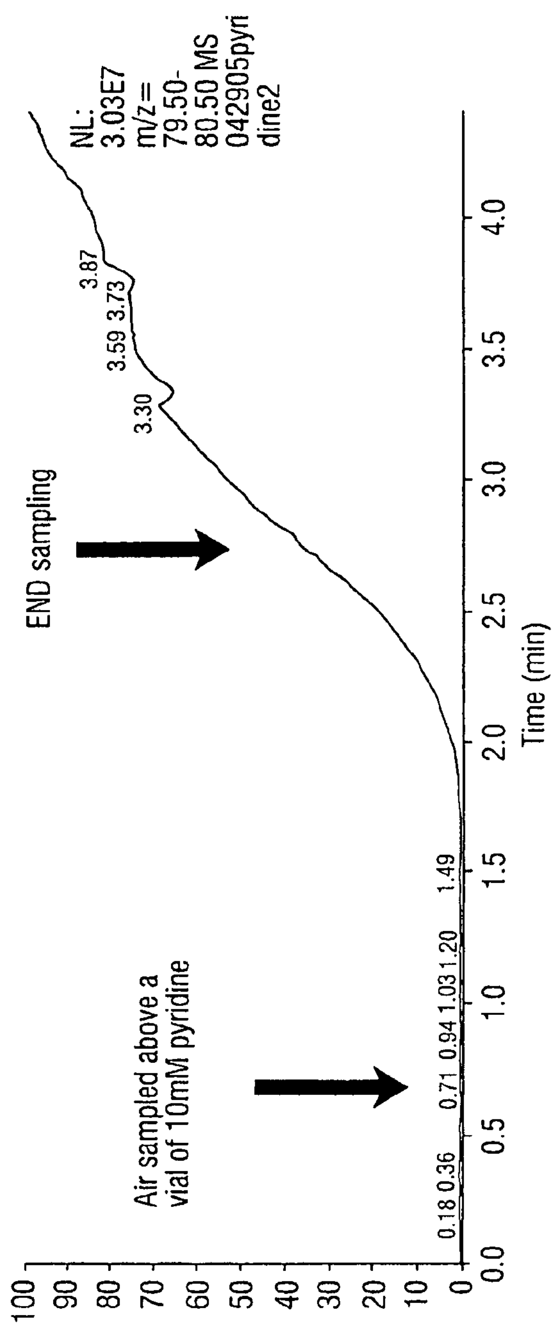

FIG. 17A illustrates the relative abundance of pyridine. FIG. 17B illustrates the results from sampling the air above a vial of 10 mM Pyridine. The signal at m/z 80 clearly goes up demonstrating the utility of the MIMS probe of the present disclosure for sampling air.

The MIMS probe of the present disclosure uses a capillary membrane (PDMS). In certain embodiments, the membrane is a concentrator due to the geometry of the membrane (the sample travels from a larger exterior surface to a smaller interior surface) unlike in pervaporization techniques. The mobile phases flow counter to one another which also acts to increase sample concentrations. Mobile phase 2 has little dead volume due to the internal design of the probe, and thus flow rates are low. The low flow rates result in low volumes and higher analyte concentrations.

The probe of the present disclosure integrates the ESI needle with the membrane. Thus, the ESI needle is part of the probe, reducing dead time and placing the ion source (both negative and positive ions are possible) near the membrane. Heating or cooling can be applied to the membrane to increase the permeation rate or adsorption rate, respectively. Liquids or gases can be used for mobile phase 1. As a result, the liquid mobile phase 2 may be the same as or different from mobile phase 1.

The probe of the present disclosure can be used a real-time concentrator unlike the solid phase extraction columns. The probe of the present disclosure maybe used with different ionization species such as protons (e.g. H+, Na+ or Li+, K+, $Cl^-$ among others). These supplemented species can be used to ionize molecules that are not typically ionized by proton addition which allow many more volatile molecules to be observed.

Flow rates may be adjusted in both the external mobile phase (mobile phase 1) and the internal mobile phase (mobile phase 2) to affect the performance (such as by enhancing the sensitivity). A low internal flow creates an increased signal due to a concentrating effect. The ESI needle allows for a small ion point source.

Voltage potentials can be added on either side of the membrane to cause an increase or decrease in permeation/migration of specific molecules in either direction across the appropriate membrane. Chemicals can also be added to mobile phase 1 to improve performance. Different solvent phases can be used on the two sides of the membrane. This is advantageous because one can use a good ESI mobile phase for mobile phase 2 such as acidic methanol while using an aqueous phase for mobile phase 1. As a result, the operator avoids the direct ESI of water solutions which is not typically very good. Other membrane materials should be possible, for example, fluorocarbon polymer types.

The probe of the present disclosure can be used for low level water analysis of semi-volatile organics, and works at atmospheric pressure unlike other MIMS probes for EI/CI sources. The probe of the present disclosure can also be used for air analysis. Finally, a multi-tage probe having more than one membrane is possible.

While the present invention has been described in conjunction with preferred embodiments thereof, those of ordinary skill in the art will recognize that many modifications and variations are possible. The present disclosure is intended to cover such modifications and variations, and is intended to be limited only by the scope of the following claims.

What is claimed is:

1. A probe, comprising:

a first flow path;

a second flow path formed by a membrane, said membrane separating said first and second flow paths, said membrane being a tubular membrane carried within a cylinder such that a space between an outside diameter of said membrane and an inside diameter of said cylinder defines said first flow path, said second flow path being formed by said tubular membrane, a liquid phase flowing in said second flow path within the tubular membrane in an opposite direction as material flowing in the first flow path between the tubular membrane and the cylinder; and a needle connected to said membrane to form a part of said second flow path;

an electrode configured to apply a voltage across the membrane;

wherein the liquid phase flows in said second flow path and is ionized at the end of said second flow path;

wherein the electrode is in contact with the liquid phase flowing in said second flow path;

wherein a flow rate in said second flow path is less than a flow rate in said first flow path.

2. The probe of claim 1 wherein said tube is wrapped around a heated support block.

3. The probe of claim 1 wherein said membrane is a tubular membrane wrapped around a support grid.

4. The probe of claim 1 wherein said membrane is a spiral wound tubular membrane.

5. The probe of claim 1 additionally comprising means for heating or means for cooling the probe.

6. The probe of claim 1 wherein a liquid or gaseous mobile phase flows in said first flow path, and a liquid mobile phase flows in said second flow path, said probe additionally comprising means for inserting additives into one or both of said mobile phases.

7. The probe of claim 1 additionally comprising a second membrane defining a third flow path, and wherein said needle is integrated with said second membrane to form a part of said third flow path.

8. A method of operating a probe, comprising:

flowing a material in a first flow path;

flowing a liquid phase in a second flow path formed by a membrane, said first and second flow paths separated by said membrane, said membrane being a tubular membrane carried within a cylinder such that a space between an outside diameter of said membrane and an inside diameter of said cylinder defines said first flow path, said second flow path being formed by said tubular membrane, the liquid phase flowing in said second flow path within the tubular membrane in an opposite direction as the material flowing in the first flow path between the tubular membrane and the cylinder;

applying a voltage across the membrane using an electrode that is in contact with the liquid phase flowing in said second flow path; and transferring the liquid phase at the end of said second flow path directly to an ionization region of a mass spectrometer;

wherein the liquid phase is ionized at the end of said second flow path;

wherein a flow rate in said second flow path is less than a flow rate in said first flow path.

9. The method of claim 8 wherein said material flowing in said first flow path is one of a liquid or a gas.

10. The method of claim 8 wherein said material flowing in said first fluid path flows in a direction opposite of a direction of flow of the fluid in said second fluid path.

11. The method of claim 8 additionally comprising one of heating or cooling the probe.

12. The method of claim 8 wherein the voltage is applied to produce one of negative or positive ions.

13. The method of claim 8 additionally comprising inserting additives into one or both of the material flowing in the first flow path and the fluid flowing in the second flow path.

14. The method of claim 8 wherein said ionizing includes electrospray ionization, atmospheric pressure photo-ionization, atmospheric pressure chemical ionization, or inductively coupled plasma ionization.

15. A method of operating a probe inserted in vivo in a first flow path, comprising;

flowing a liquid through a second flow path, said second flow path having a section formed by a membrane, said membrane being a tubular membrane carried within a cylinder such that a space between an outside diameter of said membrane and an inside diameter of said cylinder defines said first flow path, said second flow path being formed by said tubular membrane, the liquid phase flowing in said second flow path within the tubular membrane in an opposite direction as the material flowing in the first flow path between the tubular membrane and the cylinder;

inserting said membrane section of said second flow path in vivo into said first flow path;

applying a voltage across the membrane using an electrode that is in contact with the liquid flowing in said second flow path; and transferring the liquid at the end of said second flow path to an ionization region of a mass spectrometer;

wherein the liquid is ionized at the end of said second flow path.

16. The probe of claim 1 wherein a liquid or gaseous mobile phase flows in said first flow path, and a liquid mobile phase flows in said second flow path.

* * * * *